(12) United States Patent
Leung et al.

(10) Patent No.: US 8,431,744 B2
(45) Date of Patent: Apr. 30, 2013

(54) SOLVENT-FREE PREPARATION OF MAGNESIUM FORMATE-BASED POROUS METAL-ORGANIC FRAMEWORK

(75) Inventors: Emi Leung, Somerset, NJ (US); Ulrich Müller, Neustadt (DE); Gerhard Cox, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/257,348

(22) PCT Filed: Mar. 18, 2010

(86) PCT No.: PCT/EP2010/053494
§ 371 (c)(1),
(2), (4) Date: Sep. 19, 2011

(87) PCT Pub. No.: WO2010/106121
PCT Pub. Date: Sep. 23, 2010

(65) Prior Publication Data
US 2012/0016160 A1    Jan. 19, 2012

(30) Foreign Application Priority Data

Mar. 20, 2009    (EP) .................................. 09155685

(51) Int. Cl.
*C07C 53/00*    (2006.01)

(52) U.S. Cl.
USPC ........................................................ 562/609

(58) Field of Classification Search .................. None
See application file for complete search history.

(56) References Cited

FOREIGN PATENT DOCUMENTS

| KR | 2005-0052929 | 6/2005 |
|---|---|---|
| WO | WO-2006/018866 | 2/2006 |
| WO | WO-2008/096985 | 8/2008 |

OTHER PUBLICATIONS

Rood et al., Inorg. Chem. 2006, 45, 5521-5528.*
PCT International Search Report for PCT/EP2010/053494, mailed Jun. 18, 2010, 3 pages.
XP002583476 Thomson Scientific, London, GB, 2 pgs, 2006.
Gorski, A. et al., "Origin of Organic Gaseous Products Formed in the Thermal Decomposition of Formates", *Journal of Thermal Analysis*, vol. 32 1987, 1243-1251.
Kendall, James et al., "Compound Formation and Solubility in Systems of the Tupe, Formic Acid: Metal Formate", *J. Am. Chem. Soc.*, vol. 43, No. 7 1921, 1470-1481
Malard, C. et al., "Structure et stabilite thermique des deux formes du formiate de magnesium dihydrate", *Journal of Solid State Chemistry*, vol. 41, No. 1 1982, 67-74.
Rood, Jeffrey A. et al., "Synthesis, Structural Characterization, Gas Sorption and Guest-Exchange Studies of the Lightweight, Porous Metal-Organic Framework [Mg3(O2CH)6]", *Inorganic Chemistry, American Chemical Society*, vol. 45, No. 14 Jan. 2006, 5521-5528.

* cited by examiner

*Primary Examiner* — Karl J Puttlitz
(74) *Attorney, Agent, or Firm* — Servilla Whitney LLC

(57) ABSTRACT

The present invention relates to a process for preparing a magnesium formate-based porous metal-organic framework, which comprises the steps
(a) addition of magnesium or magnesium oxide to formic acid;
(b) stirring of the reaction mixture at at least 75° C.;
(c) isolation of the solid from the resulting suspension by filtration.

18 Claims, No Drawings

SOLVENT-FREE PREPARATION OF MAGNESIUM FORMATE-BASED POROUS METAL-ORGANIC FRAMEWORK

CROSS-REFERENCE TO RELATED APPLICATIONS

This application is the National Stage entry of PCT/EP2010/053494, filed on Mar. 18, 2010, which claims priority to European Patent application number 09155685.2, filed on Mar. 20, 2009, both of which are incorporated herein by reference in their entireties.

FIELD

The present invention relates to a process for preparing a magnesium formate-based porous metal-organic framework.

BACKGROUND

The present invention relates to a process for preparing a magnesium formate-based porous metal-organic framework.

Magnesium formate as porous metal-organic framework represents an interesting metal-organic coordination polymer which, owing to its porosity, is suitable for the adsorption of gases.

A closer study of this material has been carried out, for example, by J. A. Rood et al., Inorg. Chem. 45 (2006), 5521-5528.

Likewise, the preparation of magnesium formate metal-organic framework and also its use for the storage of methane is described in the international patent application number PCT/EP2009/053130.

In the abovementioned prior art, the framework is prepared in N,N-dimethylformamide as solvent.

Despite the good results in the preparation of the magnesium formate-based porous metal-organic framework, there is a need for further processes which, in particular, avoid the inclusion of solvents such as DMF and give the desired framework in good yields and in a very simple way.

It is therefore an object of the present invention to provide such a process.

SUMMARY

According to one or more embodiments, provided is a process for preparing a magnesium formate-based porous metal-organic framework, the process comprising: addition of magnesium or magnesium oxide to formic acid; stirring of the reaction mixture at at least 75° C.; and isolation of the solid from the resulting suspension by filtration.

DETAILED DESCRIPTION

The object is achieved by a process for preparing a magnesium formate-based porous metal-organic framework, which comprises the steps
(a) addition of magnesium or magnesium oxide to formic acid;
(b) stirring of the reaction mixture at at least 75° C.;
(c) isolation of the solid from the resulting suspension by filtration.

It has been found that a solvent-free synthesis leads to good results, with the formic acid present in liquid form functioning both as reagent and as solvent. Such preparative processes are typically referred to as "solvent-free" since no liquid which does not participate in the reaction and is usually present in a large excess compared to the reactants is used.

The term "magnesium formate-based" is intended to indicate that the skeleton of the porous metal-organic framework is made up of formate anions and magnesium cations. Nevertheless, part of the formate can also be present in protonated form, so that the framework can also have "defects". Furthermore, the metal-organic framework can, owing to its porosity, comprise acetic acid or formate or other substances in the pores, but these are not to be regarded as part of the framework.

In step (a) of the process of the invention, magnesium or magnesium oxide is added to formic acid.

The addition is preferably carried out under a protective gas atmosphere such as an argon atmosphere. This applies particularly when magnesium is used. If metallic magnesium is used, this is preferably present in the form of magnesium turnings. The molar ratio of formic acid to magnesium or magnesium oxide preferably corresponds to an at least 2.5-fold molar excess. Further preference is given to the excess being at least 5-fold.

The purity of the formic acid is preferably at least 95%, more preferably at least 98%, even more preferably at least 99%. In particular, pure formic acid is used. The formic acid is preferably water-free.

Particularly when magnesium oxide is used, cooling can be necessary in step (a) because of the exothermic reaction. The addition is preferably carried out so that the temperature is less than 100° C., in particular from 50 to 80° C.

After the addition is complete, the reaction mixture formed is stirred in step (b) of the process of the invention. This is preferably carried out for at least 30 minutes, more preferably at least 45 minutes and in particular at least one hour. It is preferably carried out for less than 10 hours, more preferably less than 7.5 hours and in particular less than 5 hours.

The reaction can be carried out under superatmospheric pressure so that temperatures higher than the boiling point of formic acid are possible. However, the pressure is preferably not more than 2 bar (absolute). The pressure is more preferably not more than 1230 mbar (absolute). The reaction particularly preferably takes place at atmospheric pressure. However, slightly superatmospheric or subatmospheric pressures can occur as a result of the apparatus. For the purposes of the present invention, the term "atmospheric pressure" therefore refers to the temperature range from 150 mbar below to 150 mbar above the actual prevailing atmospheric pressure.

The stirring in step (b) is carried out at a temperature of at least 75° C. However, the temperature is preferably at least 90° C. The temperature is more preferably not more than 110° C., with a temperature range from 95 to 105° C. being particularly preferred. The stirring in step (b) of the process of the invention is very particularly preferably carried out under reflux, in particular at atmospheric pressure.

After step (b) of the process of the invention, a filtration step is carried out in step (c) of the process of the invention. Owing to the formation of the magnesium formate-based porous metal-organic framework, a suspension has been formed and the solid is accordingly separated off by filtration. The filtration is preferably carried out in the presence of a solvent. This solvent can be added before filtration, after filtration or during filtration of the suspension. Preference is given to taking up the suspension in a solvent and filtering the resulting mixture. The solvent is preferably acetone.

EXAMPLES

Example 1

Preparation of the Magnesium Formate-Based Metal-Organic Framework Using Metallic Magnesium

| 1) | 5 g | of magnesium turnings | (24.3 g/mol) = | 205.8 mmol |
| 2) | 100 g | of formic acid | (46.0 g/mol) = | 2174 mmol | a) Synthesis: Formic acid is placed under argon in a reaction vessel and magnesium turnings are added a little at a time over a period of 1 hour (exothermic to 40° C.). The mixture is stirred for another 2 hours (temperature increase to 55° C., solution becomes turbulent). The mixture is then heated to reflux (RF) temperature and boiled under reflux for 1 hour.

b) Work-up: The suspension formed is stirred into 250 ml of acetone at room temperature and filtered and the solid is washed twice with 100 ml each time of acetone.

c) Drying: The framework is dried at 130° C. and 50 mbar in a porcelain dish for 16 hours in a vacuum drying oven.
Color: colorless
Yield: 21.3 g
Element analysis C: 20.8% by weight, H: 1.8% by weight, O: 56% by weight, Mg: 21.2% by weight
BET 583 $m^2/g$ by the Langmuir method

Example 2

Preparation of the Magnesium Formate-Based Metal-Organic Framework Using Magnesium Oxide

| 1) | 16.6 g | of magnesium oxide | (40.3 g/mol) = | 412 mmol |
| 2) | 120 g | of formic acid | (46.0 g/mol) = | 2609 mmol | a) Synthesis: Formic acid is placed in a 0.25 l four-neck flask and magnesium oxide is carefully added with gentle cooling (strongly exothermic to 75° C.). The mixture is then heated to 100° C. and stirred at 100° C. for 1 hour.

b) Work-up: The thick suspension formed is stirred into 300 ml of acetone at room temperature and filtered and the solid is washed twice with 200 ml each time of acetone (readily filterable).

c) Drying: The framework is dried at 130° C. and 50 mbar in a porcelain dish for 16 hours in a vacuum drying oven.
Color: colorless
Yield: 42.3 g
Element analysis C: 20.9% by weight, H: 1.8% by weight, O: 56% by weight, Mg: 21.0% by weight
BET 556 $m^2/g$ by the Langmuir method

The invention claimed is:

1. A process for solvent-free preparing a magnesium formate-based porous metal-organic framework, which comprises the steps:
   (a) addition of magnesium or magnesium oxide to formic acid to provide a reaction mixture;
   (b) stifling of the reaction mixture at at least 75° C. to form a suspension comprising a solid; and
   (c) isolation of the solid from the resulting suspension by filtration.

2. The process according to claim 1, wherein formic acid is used in an at least 2.5 fold molar excess based on the magnesium.

3. The process according to claim 1, wherein the magnesium comprises magnesium turnings.

4. The process according to claim 1, wherein the addition is carried out under a protective gas atmosphere.

5. The process according to claim 1, wherein the formic acid has a purity of at least 95%.

6. The process according to claim 1, wherein stirring is carried out for at least 30 minutes.

7. The process according to claim 1, wherein stirring is carried out under atmospheric pressure.

8. The process according to claim 1, wherein stirring is carried out at at least 90° C.

9. The process according to claim 1, wherein the suspension formed is brought into contact with a solvent before filtration or during filtration.

10. The process according to claim 9, wherein the solvent is acetone.

11. The process according to claim 1, wherein formic acid is used in an at least 5 fold molar excess based on the magnesium.

12. The process according to claim 1, wherein addition is carried out at a temperature less than 100° C.

13. The process according to claim 6, wherein stirring is carried out under atmospheric pressure and at at least 90° C.

14. The process according to claim 1, wherein stirring is carried out under reflux.

15. The process according to claim 13, wherein stirring is carried out under reflux.

16. The process according to claim 4, wherein the protective gas atmosphere comprises argon.

17. The process according to claim 3, wherein the addition is carried out under a protective gas atmosphere.

18. The process according to claim 17, wherein the protective gas atmosphere comprises argon.

* * * * *